United States Patent [19]

Swallow

[11] 4,024,183

[45] May 17, 1977

[54] ANTIVIRAL GUANIDINO-URLIDO-BENZENE COMPOUNDS

[75] Inventor: Douglas Lintin Swallow, Macclesfield, England

[73] Assignee: Imperial Chemical Industries Limited, London, England

[22] Filed: Oct. 6, 1975

[21] Appl. No.: 620,049

Related U.S. Application Data

[63] Continuation-in-part of Ser. No. 209,381, Dec. 17, 1971, abandoned.

[30] Foreign Application Priority Data

Jan. 7, 1971 United Kingdom ................. 777/71

[52] U.S. Cl. ...................... 260/553 A; 260/501.14; 260/552 R; 260/553 C; 260/565; 424/316; 424/317; 424/322
[51] Int. Cl.² ................ C07C 127/19; A61K 31/17
[58] Field of Search ...... 260/553 A, 553 C, 501.14, 260/565

[56] References Cited

UNITED STATES PATENTS 3,560,566  2/1971  Marxer ....................... 260/553 C X
3,673,241  6/1972  Marxer ....................... 260/553 C X

OTHER PUBLICATIONS

Stuart–Harris et al., *The Background to Chemotherapy of Virus Diseases*, Charles Thomas, pp. 46–82 (1964).
Heath et al., *Modern Trends in Medical Virology*, Appleton–Century–Crafts, pp. 54–56 (1967).
Burnet et al., *The Viruses, Biochemical, Biological and Biophysical Properties*, vol. 3, Academic Press, pp. 220–222 (1959).
Conn, *Current Therapy* 1973, 25th ed., W. B. Saunders Co., pp. 154–156 (1973).
Bucknell et al., CA 80: 104407f (1974).
Swallow, CA 78: 124323n (1973).

*Primary Examiner*—Robert V. Hines
*Assistant Examiner*—Thomas A. Waltz
*Attorney, Agent, or Firm*—Cushman, Darby & Cushman

[57] ABSTRACT

The disclosure relates to novel aromatic compounds which possess antiviral activity, to processes for their manufacture and to a method of selectively inhibiting rhinovirus growth in the presence of other viruses.

5 Claims, No Drawings

ANTIVIRAL GUANIDINO-URLIDO-BENZENE COMPOUNDS

This application is a continuation in part of application Ser. No. 209,381, filed 17 Dec. 1971, now abandoned This invention relates to new aromatic compounds which possess antiviral activity, and in particular it relates to such compounds which are active against rhinoviruses.

According to the invention there is provided an aromatic compound of the formula:

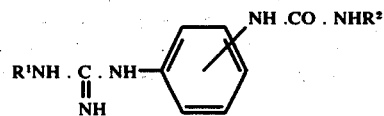  I wherein either $R^1$ is the ethyl radical, $R^2$ is a bromophenyl radical and the group —NH.CO.NHR$^2$ is in the meta-position, or $R^1$ is the isopropyl, isobutyl, isopentyl or phenyl radical, $R^2$ is a chlorophenyl, bromophenyl, nitrophenyl, ethoxyphenyl or tolyl radical and the group —NH.CO.NHR$^1$ is in the meta-or para-position, or $R^1$ is a chlorophenyl radical, $R^2$ is an alkyl radical of 3 to 10 carbon atoms and the group —NH.CO.NHR$^2$ is in the meta-position, or $R^1$ is a chlorophenyl or tolyl radical, $R^2$ is a phenyl or o-chlorophenyl radical and the group —NH.CO.NHR$^2$ is in the para-position, and the acid addition salts thereof.

A suitable value for $R^1$ when it is a chlorophenyl radical is, for example, the 4-chlorophenyl radical. A suitable value for $R^2$ when it is a chlorophenyl radical is, for example, the 2-, 3- or 4-chlorophenyl radical.

A suitable value for $R^2$ when it is a bromophenyl, nitrophenyl, ethoxyphenyl or tolyl radical is, for example, the 4-bromophenyl, 4-nitrophenyl, 4-ethoxyphenyl or 4-tolyl radical.

A suitable value for $R^2$ when it is an alkyl radical of 3 to 10 carbon atoms is, for example, an alkyl radical of 4 to 8 carbon atoms, for example the n-butyl, isobutyl or n-octyl radical.

A suitable acid addition salt is, for example, a salt with an inorganic acid, for example a hydrochloride, sulphate or phosphate, or a salt with a carboxylic acid, for example an acetate, benzoate, tartrate, adipate, lactate, citrate, gluconate, oxalate or succinate, or with a sulphonic acid, for example a methanesulphonate or toluene-p-sulphonate.

A preferred group of compounds of the invention comprises those compounds wherein $R^1$ is the isobutyl radical, $R^2$ is a chlorophenyl, bromophenyl, nitrophenyl, ethoxyphenyl or tolyl radical, and the group —NH.CO.NHR$^2$ is in the meta-position.

Particular compounds -m-chlorophenylureido)benzene, the invention are 1-(3-ethylguanidino)-3-(3-p-bromophenylureido)benzene, 1-(3-isopropylguanidino)-3-(3-p-chlorophenyluredio)benzene, 1-(3-isobutylguanidino)-3-(3-p-chlorophenylureido)benzene, 1-(3-isobutylguanidino)-3-(3-m-chlorophenylurido)benzene, 1-(3-isobutylguanidino)-3-(3-o-chlorophenylureido)benzene, 1-(3-isobutylguanidino)-3-(3-p-bromophenyluredio)benzene, 1-(3-isobutylguanidino)-3-(3-p-nitrophenylureido)benzene, 1-(3-isobutylguanidino)-3-(3-p-tolylureido)benzene, 1-(3-isobutylguanidino)-3-(3-p-ethoxyphenylureido)benzene, 1-(3-phenylguanidino)-3-(3-p-chlorophenylureido)benzene, 1-(3-p-chlorophenylguanidino)-3-(3-n-butyluredio)benzene, 1-(3-p-chlorophenylguanidino)-3-(3-isobutylureido)benzene, 1-(3-p-chlorophenylguanidino)-3-(3-n-octylureido)benzene, 1-(3-iso-propylguanidino)-4-(3-p-chlorophenyluredio)benzene, 1-(3-isobutylguanidino)-4-(3-p-chlorophenylureido)benzene, 1-(3-isopentylguanidino)-4-(3-p-chlorophenylureido)benzene and 1-(3-isobutylguanidino)-4-(3-p-tolylureido)benzene.

According to a further feature of the invention there is provided a process for the manufacture of the compounds of the invention which comprises:

a. the interaction of an amino compound of the formula:

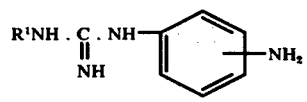  II with an isocyanate of the formula $R^2$. NCO, wherein $R^1$ and $R^2$ have the meanings stated above; or b. the reaction of a thiouredio compound of the formula:

  III with ammonia in the presence of a catalyst, wherein $R^1$ and $R^2$ have the meanings stated above; or c. the reaction of ammonia with a thiouronium salt of the formula:

  IV wherein $R^1$ and $R^2$ have the meanings stated above, $R^3$ is an alkyl radical of 1 to 4 carbon atoms or an aralkyl radical of up to 10 carbon atoms, and $Z^-$ is an anion; or d. the oxidation of a thioureido compound of the formula:

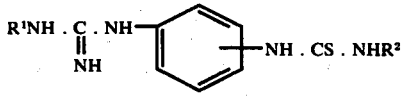  V whereafter when a salt is required, the product thus obtained is reacted with an acid.

A suitable catalyst which may be used in the process of the invention is, for example, an oxide of an element in group IIB or IVA of the periodic table, for example mercuric oxide or lead oxide, PbO.

A suitable value for $R^3$ is, for example, the methyl, ethyl or benzyl radical, and a suitable value for the anion $Z^-$ is, for example, the chloride or bromide ion.

The oxidation of the thioureido compound V may be carried out by any known means described in the chemical literature for oxiding a thiourea to the corresponding urea, for example by the action of mercuric oxide.

The process may be carried out in an inert diluent or solvent, for example pyridine for process (a) or ethanol for process (b), (c) or (d), and it may be carried out at ambient temperature or at an elevated temperature of between 25° and 100° C.

The amino compound of the formula II used as starting material in the process of the invention may be obtained from available materials by well-known chemical reactions, for example by reacting a phenylenediamine with one equivalent of an isothiocyanate of the formula R¹.NCS, and reacting the thioureidoaniline thus obtained with ethanolic ammonia in the presence of mercuric oxide.

The thioureido compound of the formula III which may be used as starting material in the process of the invention may be obtained from available materials by well-known chemical reactions, for example by reacting a thioureidoaniline of the formula:

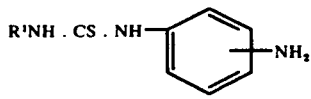

obtained as described above, with an isocyanate of the formula R².NCO.

The thiouronium salt of the formula IV which may be used as a starting material in the process of the invention may be obtained, for example, by the reaction of a thiourea of the formula III with a compound of the formula R³.Z.

The thioureido compound of the formula V which may be used as starting material in the process of the invention may be prepared from available materials by well-known chemical reactions, for example by reacting an amino compound of the formula II with an isothiocyanate of the formula R²NCS.

As stated above, the new compounds of the invention possess antiviral activity, and in particular they are active against rhinoviruses. This activity is demonstrated by a tissue culture assay in human embryo lung cells, whereby it may be shown that compounds of the invention inhibit the growth of at least 24 different rhinoviruses at a concentration of less than 12.5 µg./ml. without at the same time producing any detectablet toxic effects on the tissue culture cells.

It is well-known in this art that compounds which display antiviral activity against one virus type are generally inactive against other viruses (see, for example, "The Viruses," edited by F.M. Burnet and W.M. Stanley, Academic Press, New York, 1959, volume 3, page 221). Thus, for example 1-aminoadamantane is active only against influenza A, and $A_2$, and not against other myxo- and paramyxo- viruses (Davies et al., Science, 1964, 144, 862) and α-hydroxybenzyl benzimidazole is active only against picornaviruses and not against other ribonucleic acid (RNA) viruses (Eggers and Tamm, J. Exp. Med., 1961, 113, 657).

It is therefore evident that an inherent property of the compounds of the present invention is their ability selectively to inhibit the growth of rhinoviruses in the presence of other viruses and, alternatively, to prevent contamination of cultures of other viruses by rhinoviruses. The compounds of the present invention are therefore useful in hospital and public health laboratories for selectively inhibiting rhinovirus growth in tissue cultures, thus allowing other viruses which may be present to be detected more easily. For example, clinical specimens from patients with upper respiratory tract disease may be cultured in the presence of a compound of the invention. Rhinoviruses grow in the upper respiratory tract of man, and rhinoviruses will often be present in such specimens. Rhinovirus growth during incubation is prevented but other viruses which may be present, such as influenza, adenoviruses and respiratory syncytial virus, grow unchecked. Similarly, in the public health filed, the growth of rhinoviruses may be suppressed while other viruses such as the enteroviruses, the arborviruses, myxoviruses, and DNA-containing viruses, against which the compounds of the invention have no effect, continue to multiply normally in tissue culture.

Alternatively, the ability of the compounds of the invention selectively to inhibit the growth of rhinoviruses in the presence of other viruses provides a dianostic tool for the speedy identification of rhinoviruses in a mixed virus population.

In use the compound of the invention is added as a suspension or solution in a suitable diluent or solvent, which is generally water or the tissue culture medium, to the tissue culture under examination. The final concentration of the compound of the invention may be varied over a wide range, but is generally in the range of 0.04 to 45 µg./ml. The culture is then incubated for the appropriate period of time at the appropriate temperature before examination for viral growth.

The invention is illustrated but not limited by the following Examples:

EXAMPLE 1

Lead oxide (PbO, 0.8 g.) is added to a solution of 1-(3-isobutylthioureido)-3-(3-p-chlorophenylureido)-benzene (1.13 g.) in ethanol which has been saturated with ammonia gas (50 ml.). The mixture is stirred at room temperature for 7 days, the solids are filtered off, washed thoroughly with boiling ethanol and the combined filtrates are evaporated to dryness. The residual gum is dissolved in ethanol (5 ml.) and saturated ethereal hydrochloric acid (3 ml.) is added, followed by dry ether (150 ml.). The precipitated white solid is filtered off, washed with dry ether followed by cold isopropanol, and dried under reduced pressure, to give 1-(3-isobutylguanidino)-3-(3-p-chlorophenylureido)benzene hydrochloride, m.p. 212° C.

The 1-(3-isobutylthioureido)-3-(3-p-chlorophenylureido)benzene used as starting material may be obtained as follows:

A solution of freshly distilled p-chlorophenyl isocyanate (1.38 g.) in 10 ml. chloroform is added at room temperature in one portion to a solution of 1-isobutyl-3-(m-aminophenyl)thiourea (2.0 g.) in chloroform (30 ml.). The product precipitates rapidly and is filtered off after several hours. The filter cake is washed with chloroform and dried to give 1-(3-p-chlorophenylureido)-3-(3-isobutylthioureido)-benzene, m.p. 195°–196° C.

EXAMPLE 2

Isobutyl isocyanate (0.7 g.) is added to a solution of 1-(p-chlorophenyl)-3-(m-aminophenyl)guanidine dihydrochloride (2.0 g.) in pyridine (20 ml.) at room temperature, and the mixture is stirred for 48 hours. Then a further 0.7 g. of isobutyl isocyanate is added and the mixture is kept at 50° C. for 9 days. The pyridine is evaporated under reduced pressure and the residue is dissolved in methanol (30 ml.), the solution is boiled briefly with activated charcoal filtered and evaporated to dryness. The solid residue is dissolved in dilute hydrochloric acid and the solution is made alkaline with 10% aqueous sodium hydroxide. The precipitate is filtered off, washed with water, dried and converted to the hydrochloride by dissolving the solid in a little ethanol, adding ethereal hydrochloric acid, and precipitating the hydrochloride by the addition of an excess of dry ether. The precipitated solid is washed with a little isopropanol and there is thus obtained 1-(3-p-chlorophenylguanidino)-3-(3-isobutylureido)-benzene hydrochloride, m.p. 207°–209° C.

The 1-(p-chlorophenyl)-3-(m-aminophenyl)guanidine dihydrochloride used as starting material can be obtained in the following manner:

A solution of p-chlorophenyl isothiocyanate (39.6 g.) in chloroform (100 ml.) is added dropwise with stirring to a solution of m-phenylene diamine (25.2 g.) in chloroform (200 ml.) at room temperature. The mixture is stirred for 1 hour after the addition is complete, and the precipitated solid is filtered off, washed with chloroform and dried to give 1-(p-chlorophenyl)-3-(m-aminophenyl)thiourea, m.p. 132°–133.5° C. This product (20 g.) is dissolved in ethanol saturated with ammonia gas (300 ml.), yellow mercuric oxide (17.2 g.) is added and the mixture is stirred for 24 hours at room temperature. The black precipitate is filtered off and washed thoroughly with boiling ethanol, and the filtrate is evaporated to dryness. The residue is dissolved in chloroform, the solution is filtered and an excess of ethereal hydrochloric acid is added to the filtrate, followed by a large volume of ether. The oily precipitate is allowed to solidify, is triturated with fresh dry ether, and is filtered off and dried, to give 1-(p-chlorophenyl)-3-(m-aminophenyl)guanidine dihydrochloride, m.p. 236°–238° C.

EXAMPLE 3

1-(3-Isopropylthioureido)-3-(3-p-chlorophenylureido)-benzene (1.5 g.) is dissolved in ethanol (100 ml.) saturated with ammonia gas, and the solution stirred for 24 hours at room temperature with yellow mercuric oxide (1.02 g.). The mixture is boiled for ½ hour to coagulate the fine precipitate, and is filtered hot. The solid is washed thoroughly with 3 × 50 ml. portions of boiling ethanol, and the filtrate and washings are combined and evaporated to dryness. The remaining gum is dissolved in methanol (10 ml.) and saturated ethereal hydrogen chloride (3 ml.) is added followed by dry ether (150 ml.). The precipitated oil rapidly solidifies, is filtered off and crystallised from ethanol to give 1-(3-isopropylguanidino)-3-(3-p-chlorophenylureido)benzene hydrochloride, m.p. 224°–225° C.

The 1-(3-isopropylthioureido)-3-(3-p-chlorophenylureido)benzene used as starting material may be obtained as follows:

m-Phenylenediamine (10.8 g.) is dissolved in methylene chloride (500 ml.) at room temperature and a solution of p-chlorophenyl isocyanate (15.35 g.) in methylene chloride (50 ml.) is added dropwise with vigorous stirring. The mixture is stirred for 2 hours after the addition is complete, and the product is filtered off, washed with methylene chloride and dried. This solid thus obtained is crystallized from methanol (3 l.) to give 3-(3-p-chlorophenylureido)aniline, which slowly decomposes on heating to 310° C. without melting, but is analytically pure.

A solution of 3-(3-p-chlorophenylureido)aniline (2.0 g.) in pyridine (40 ml.) is stirred at 0° C. with isopropyl isothiocyanate (0.77 ml.). The solution is allowed to warm slowly to room temperature and is stirred for 48 hours. The solution is filtered, the pyridine is removed by distillation under reduced pressure and the residue is crystallized from methanol (300 ml.) to give 1-(3-isopropylthioureido)-3-(3-p-chlorophenylureido)benzene, m.p. 197°–198° C. with decomposition.

EXAMPLE 4

To a solution of 1-isobutyl-3-m-aminophenylguanidine dihydrochloride (19.6 g.) in pyridine (100 ml.) is added dropwise a solution of p-chlorophenyl isocyanate (11.5 g.) in pyridine (25 ml.) at room temperature. The mixture is stirred for 16 hours, and the pyridine is removed by distillation under reduced pressure. The residual gum is shaken with a mixture of ether (100 ml.) and 1% aqueous sodium hydroxide solution (10 ml.) to remove pyridine hydrochloride whereafter the product crystallizes. The solid is filtered off, washed with water and ether and dried, and recrystallized from ethanol/petroleum ether b.p. 40°–60° C. to give 1-(3-isobutylguanidino)-3-(3-p-chlorophenylureido)benzene hydrochloride, m.p. 215°–216° C.

The 1-isobutyl-3-m-aminophenylguanidine dihydrochloride used as starting material is obtained in the following manner:

Isobutyl isothiocyanate (16 g.) is added dropwise with stirring to a solution of m-phenylenediamine (17 g.) in methylene chloride (500 ml.) at room temperature. After 16 hours the solution is concentrated until crystallization begins. The mixture is diluted with benzene, and the product is filtered off, washed with benzene and dried. The 1-isobutyl-3-m-aminophenylthiourea thus obtained (23 g.) is dissolved in ethanol (250 ml.) saturated with ammonia gas, and stirred for 48 hours at room temperature with yellow mercuric oxide (28.2 g.). The mixture is filtered, the solids washed thoroughly with boiling ethanol and the combined filtrate and washings are evaporated to dryness. The residue is dissolved in a little methanol, treated with excess saturated ethereal hydrogen chloride and a large volume of dry ether. A red oil separates, which is triturated with fresh ether until solid, and the solid is filtered off and crystallized from methanol/ethyl acetate, to give 1-isobutyl-3-m-aminophenylguanidine dihydrochloride, m.p. 215° C.

EXAMPLE 5

The process described in Example 2 is repeated but using the appropriate substituted phenylaminophenylguanidine, prepared by the process described in the second part of Example 2, and the appropriate isocyanate in place of isobutyl isocyanate, to give the following compounds:

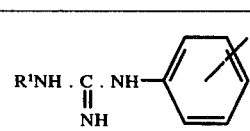

| R¹ | R² | Linkage | Crystallisation solvent | M.p. (° C.) hydrochloride |
|---|---|---|---|---|
| p-chlorophenyl | n-butyl | m | ethanol/petrol | 199–201 |
| p-chlorophenyl | n-octyl | m | ethanol/ | 180–183 |

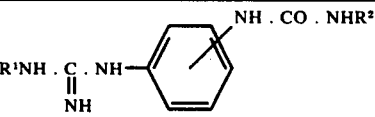

| R¹ | R² | Link-age | Crystallis-ation solvent | M.p. (° C.) hydrochloride |
|---|---|---|---|---|
| p-chlorophenyl | o-chloro-phenyl | p | petrol ethanol/ petrol | 170–175 |
| p-tolyl | phenyl | p | ethanol/ petrol | 236–238 |
| phenyl | p-chloro-phenyl | m | ethanol | 210–214 |

EXAMPLE 6

The process described in Example 6 is repeated but using the appropriate ureido-thioureido-benzene prepared by the process described in the second part of Example 6, in place of 1-(3-isopropylthioureido)-3-(3-p-chlorophenylureido)-benzene to give the following compounds:

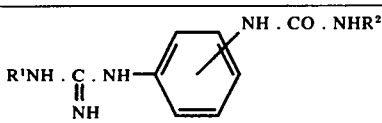

| R¹ | R² | Linkage | Crystallis-ation solvent | M.p. (° C.) hydrochloride |
|---|---|---|---|---|
| isopropyl | p-tolyl | m | methanol/ ethyl acetate | 227–230 |
| isobutyl | p-tolyl | m | ethanol | 197–198 |
| isopropyl | p-chloro-phenyl | p | ethanol | 193–194 |
| isobutyl | p-chloro-phenyl | p | ethanol | 175–177 |
| isopentyl | p-chloro-phenyl | p | ethanol | 190–191 |
| isobutyl | p-tolyl | p | methanol/ water | 223–225 |

EXAMPLE 7

The process described in Example 7 is repeated using the appropriate aminophenylguanidine, prepared by the process described in the second part of Example 7, in place of 1-isobutyl-3-m-aminophenylguanidine, and the appropriate isocyanate in place of p-chlorophenyl isocyanate to give the following compounds:

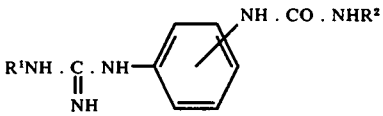

| R¹ | R² | Linkage | Crystallis-ation solvent | M.p. (° C.) hydrochloride |
|---|---|---|---|---|
| ethyl | p-bromo-phenyl | m | methanol | 231–234 |
| isobutyl | m-chloro-phenyl | m | methanol/ ethyl acetate | 218 |
| isobutyl | o-chloro-phenyl | m | methanol | 202 |
| isobutyl | p-bromo-phenyl | m | methanol/ ethyl acetate | 216–218 |
| isobutyl | p-nitro-phenyl | m | methanol/ ethyl | 239–241 |

| R¹ | R² | Linkage | Crystallis-ation solvent acetate | M.p. (° C.) hydrochloride |
|---|---|---|---|---|
| isobutyl | p-ethoxy-phenyl | m | ethanol/ 40–60 petrol | 166–167 |

EXAMPLE 8

1-(3-Isobutylguanidino)-3-(3-p-chloro-phenylureido)-benzene hydrochloride (33.2g.) is suspended in ethyl acetate and stirred vigorously with a solution of caustic soda (4g.) in distilled water (200 ml.) at room temperature until all the solid has dissolved. The organic phase is carefully separated and stirred with a solution of gluconolactone (11.9 g.) in distilled water (250 ml.) for 16 hours. The aqueous phase is separated and freeze-dried to give 1-(3-isobutylguanidino)-3-(3-p-chlorophenylureido)benzene gluconate, crystallized from a small volume of absolute ethanol, m.p. 144°–146° C.

EXAMPLE 9

Human embryonic lung cells growing in Eagles medium in 4 inches × ½ inch glass tubes were doubly infected with 100 TCD$_{50}$ of herpes simplex type 1 virus and 100 TCD$_{50}$ of rhinoviruses type 2 and incubated at 33° C. Two days later, the cells were seen to be degenerating due to the growth of the viruses and the culture fluids were shown by infectivity titrations to contain at least a hundred times more of each virus than the original inoculum.

In a parallel experiment the culture medium was prepared containing 1-(3-isobutylguanidino)-3-(3-p-chlorophenylureido)benzene hydrochloride at a concentration of 5 μg./ml. This medium was added to doubly infected cell cultures which were incubated at 33° C. for 2 days, as above. The cells were then again seen to be degenerating due to virus growth, but the culture fluids were shown to contain a high concentration of herpesvirus only, the growth of rhinovirus having been suppressed.

What we claim is:

1. A compound of the formula:

[structure]

selected from the group consisting of those compounds wherein R¹ is ethyl, R² is bromophenyl, and the group —NH.CO.NHR² is in the meta-position, those compounds wherein R¹ is isopropyl, isobutyl, isopentyl or phenyl, R² is chlorophenyl, bromophenyl, nitrophenyl, ethoxyphenyl or tolyl and the group —NH.CO.NHR² is in the meta- or para-position, those compounds wherein R¹ is chlorophenyl, R² is alkyl of 3 to 10 carbon atoms and the group —NH.CO.NHR² is in the meta-position, and those compounds wherein R¹ is chlorophenyl or tolyl, R² is phenyl or o-chlorophenyl and the group —NH.CO.NHR² is in the para-position, and the acid addition salts thereof.

2. The compound of claim 1 wherein R¹ is isopropyl, isobutyl, isopentyl or phenyl, R² is 2-, 3- or 4-chlorophenyl, 4-bromophenyl, 4-nitrophenyl, 4-ethoxyphenyl or 4-tolyl, and the group —NH.CO.NHR² is in the meta- or para-position.

3. The compound of claim 1 wherein R¹ is isobutyl, R² is chlorophenyl, bromophenyl, nitrophenyl, ethoxyphenyl or tolyl, and the group —NH.CO.NHR² is in the meta- or para-position.

4. 1-(3-Isobutylguanidino)-3-(3-p-chlorophenylureido)-benzene and the acid addition salts thereof.

5. A compound selected from 1-(3-ethylguanidino)-3-(3-p-bromophenylureido)benzene, 1-(3-isopropylguanidino)-3-(3-p-tolylureido)benzene, 1-(3-isobutylguanidino)-3-(3-m-chlorophenylureido)benzene, 1-(3-isobutylguanidino)-3-(3-o-chlorophenylureido)benzene, 1-(3-isobutylguanidino)-3-(3-p-bromophenylureido)benzene, 1-(3-isobutylguanidino)-3-(3-p-nitrophenylureido)benzene, 1-(3-isobutylguanidino)-3-(3-p-ethoxyphenylureido)benzene, 1-(3-isobutylguanidino)-3-(3-p-tolylureido)benzene, 1-(3-phenylguanidino)-3-(3-p-chlorophenylureido)benzene, 1-(3-p-chlorophenylguanidino)-3-(3-isobutylureido)benzene, 1-(3-p-chlorophenylguanidino)-3-(3-n-octylureido)benzene, 1-(3-isopropylguanidino)-4-(3-p-chlorophenylureido)benzene, 1-(3-isobutylguanidino)-4-(3-p-chlorophenylureido)-benzene, 1-(3-isopentylguanidino)-4-(3-p-chlorophenylureido)benzene and 1-(3-isobutylguanidino)-4-(3-p-tolylureido)benzene and the acid addition salts thereof.

* * * * *

UNITED STATES PATENT OFFICE
CERTIFICATE OF CORRECTION

Patent No. 4,024,183      Dated May 17, 1977

Inventor(s) Douglas Lintin Swallow

It is certified that error appears in the above-identified patent and that said Letters Patent are hereby corrected as shown below:

In Item [54] the title should read:

--ANTIVIRAL GUANIDINO-UREIDO-BENZENE COMPOUNDS--

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*